United States Patent [19]

Choudhry

[11] Patent Number: 4,805,468
[45] Date of Patent: Feb. 21, 1989

[54] FIBER COLLECTION AND STORAGE DEVICE

[75] Inventor: Muhammad Y. Choudhry, Stone Mountain, Ga.

[73] Assignee: The United States of America as represented by the Secretary of the Army, Washington, D.C.

[21] Appl. No.: 155,405

[22] Filed: Feb. 12, 1988

[51] Int. Cl.⁴ .......................... G01N 33/36; G01N 1/04
[52] U.S. Cl. ................................ 73/864.71; 33/1 B; 26/70; 73/864; 73/864.91
[58] Field of Search ............... 73/864.71, 864, 864.91, 73/159, 104; 26/70; 33/1 B, 1 BB

[56] References Cited

U.S. PATENT DOCUMENTS

| | | | |
|---|---|---|---|
| 1,965,337 | 7/1934 | Geyer | 33/1 B |
| 2,236,373 | 3/1941 | Kowalski | 73/104 X |
| 3,430,496 | 3/1969 | Swanberg et al. | 73/864.71 |
| 4,144,760 | 3/1979 | Schlüeter et al. | 73/864.71 |

OTHER PUBLICATIONS

*J. Forens. Sci. Soc.;* vol. 15: No. 1, Jan. 1975, pp. 17-27, "The Transfer of Fibres Between Clothing Materials During Simulated Contacts and their Persistence During Wear—Part I—Fibre Transference" by C. A. Pounds et al. and No. 2, Apr. 1975, pp. 127-132, The Recovery of Fibres from the Surface of Clothing for Forensic Examinations, by C. A. Pounds.
*Forensic Science: An Introduction to Criminalistics;* pp. 146-152; 1983; McGraw-Hill, New York; by Peter R. DeForest et al.
*Journal of Forensic Sciences:* vol. 26, No. 3, Jul. 1981, pp. 560-563, "An Improved Method for Rapid and Accurate Scanning of Fibers on Tape", by M. C. Grieve et al.
Vol. 29, No. 1, Jan. 1984, pp. 55-65, "Fiber Evidence: Laboratory Methods and Observations from Casework", by Wilkaon Fong.
Vol. 29, No. 4, Oct. 1984, Letters to the Editor: pp. 955-956, "Discussion of Fiber Evidence: Laboratory Methods and Observations from Casework", by Michael C. Grieve and pp. 957-959, Authors Response by Wilkaan Fong.

*Primary Examiner*—Tom Noland
*Attorney, Agent, or Firm*—Anthony T. Lane; William V. Adams; Werten F. W. Bellamy

[57] ABSTRACT

This invention is directed to a fiber collection and storage device comprising in combination (1) a stable, transparent carrier base material preponderate on a surface thereof with a grid and label, the grid having uniquely identified areas wherein collected fibers are located and the label providing identification indicia, (2) an adhesive layer is disposed on the surface of the carrier base material, the adhesive layer being capable of collecting and recovering transferred-fibers from textile articles, and (3) a transparent and flexible cover for occlusively covering the adhesive layer and the method for using the device.

10 Claims, 2 Drawing Sheets

|   | A | B | C | D | E | F | G | H | I | J |
|---|---|---|---|---|---|---|---|---|---|---|
| 1 | | | | | | | | | | |
| 2 | | | | | | | | | | |
| 3 | | | | | | | | | | |
| 4 | | | | | | | | | | |
| 5 | | | | | | | | | | |
| 6 | | | | | | | | | | |
| 7 | | | | | | | | | | |
| 8 | | | | | | | | | | |
| 9 | | | | | | | | | | |
| 10 | | | | | | | | | | |

VICTIM____ SUSPECT____ FRONT____ SHIRT____
CRIME SCENE              BACK____ PANTS____
CASE NO._____ INSIDE____ BLOUSE____
EXHIBIT NO._____ OUTSIDE____
INITIALS_____ DATE____

FIG. 1

FIBER COLLECTION AND STORAGE DEVICE

FIELD OF THE INVENTION

This invention relates to a simple, rapid, efficient and reliable device for collecting and storing transferred-fibers from textile articles, using a novel fiber collection and storage device.

BACKGROUND OF THE INVENTION

A variety of imperfect and/or inadequate techniques are available for the purpose of collecting fibers from clothing articles (textiles).

The success of any criminal investigation is often dependent upon the recovery of trace evidential material for subsequent analytical or comparative examinations or both. Textile fibers are one of the most common types of transfer evidence encountered in forensic science. Transfer of fibers occurs, according to Locard's Exchange Principle, Pounds, C. A. and Smalldon, K. W., "The Transfer of Fibres Between Clothing Materials During Simulated Contacts and their Persistence During Wear," *Journal of the Forensic Science Society*, Vol. 15. No. 1, January 1975, pp. 17-27 results when one textile article is contacted with another. The transferred-fibers are generally invisible to the naked eye. However, the collection and recovery of these transferred-fibers from the textile articles is an important aspect in cases involving fiber evidence.

Since the introduction of the vacuum sweeping technique by Kirk, P. L., *Crime Investigation, Interscience Publishers,* New York, 1953, pp. 100-108 and 629-635 in 1953, several methods, including shaking, brushing, scraping, and high and low adhesive tape lifting, have been reported for the collection of transferred-fibers from clothing articles. The collection efficiency and the associated limitations of each of these methods have been evaluated by Pounds, C. A., "The Recovery of Fibres from the Surface of Clothing Submitted for Forensic Examination," *Journal of Forensic Sciences,* Vol. 15, No. 2, April 1975, pp. 127-132.

The process of collection is followed by localization and separation of significant fibers. Many available techniques are capable of collecting fibers. However, the fiber recovery process is time-consuming, tedious, and often frustrating. Even the improved procedures such as the use of (1) adhesive rollings, described by Fong, W., in "Fiber Evidence: Laboratory Methods and Observations from Casework," *Journal of Forensic Sciences,* Vol. 29, No. 1, January 1984, pp. 55-63 ; and (2) tape scanners, described by Grieve, M. C. and Garger, E. F., in "An Improved Method for Rapid and Accurate Scanning of Fibers on Tape," *Journal of Forensic Sciences,* Vol. 26, No. 3, July 1981, pp. 560-563, have failed to gain popularity as a result of associated drawbacks including the loss of area specificity, Grieve, M. C., "Discussion of 'Fiber Evidence: Laboratory Methods and Observations from Casework'," *Journal of Forensic Sciences,* Vol. 29, No. 4, October 1984, pp. 955-956, with the rolling technique and the possibility of contamination of tape strips as has been pointed out by the developer of the technique, Grieve, M. C. and Garger, E. F., "An Improved Method for Rapid and Accurate Scanning of Fibers on Tape," *Journal of Forensic Sciences,* Vol. 26, No. 3, July 1981, pp. 560-563, and others, Fong, W., "Author's Response to 'Discussion of Fiber Evidence: Laboratory Methods and Observations from Casework'," *Journal of Forensic Sciences,* Vol. 29, No. 4, October 1984, pp. 957-959. Accordingly, prior to this invention, a long felt need existed in the field of forensic science to develop an improved method for the collection of fibers in complex cases which is effective and rapid and has the ability to maintain area specificity.

SUMMARY OF THE INVENTION

The adhesive bed component of the fiber collection and storage device consists of a transparent polymeric sheet (100 by 130 mm or other sizes) printed with a suitable grid and label. The grid area is covered with a thin layer of an appropriate adhesive material such as that used in the manufacture of adhesive tapes. (Similar or equivalent adhesive material is presently used in the manufacturing of 3M 810 Magic or 665 double coated Scotch tapes). The device consists of a clear plastic covering attached to the adhesive lifting medium. As such, the plastic covering sheet will protect the adhesive lifting surface from any contamination. In addition, this transparent plastic covering will make the handling and storage of the device more convenient than using a document protector. The actual sketch of the device is shown in FIG. 1.

This device will enable crime investigation personnel to make rapid, effective and convenient collection and recovery of fibers, and/or hair, or other trace evidential material from apparel and other surfaces.

The proposed adhesive bed technique utilized in the present fiber collection and storage device is simple, effective, practical, and time saving. The advantages of this technique over previously described procedures are as follows:

1. Since the present fiber collection and storage device has a large surface, each contact with the textile material covers a large area (as compared to using narrow strips of adhesive tape). Thus, a large piece of clothing is processed rapidly and completely. The chances of leaving out unexplored areas will be much lower than would exist if individual strips of adhesive tape were used. Further, in the case of articles with course texture, collection of fibers will not be a problem (compared to the individual tape lift method) since appropriate pressure can be applied to recover the suspect fibers from such areas.

2. Since the Double Coated tape used to construct the device is not highly adhesive and is comparable to the conventionally used 3M Scotch 810 Magic tape in adhesive thickness and material, the problem of picking up a greater number of background fibers during collection does not arise.

3. Because the fiber collection and storage device is transparent, the search for matching fibers is relatively easy and rapid.

4. Since the present device stays flat (unlike the individual strips of adhesive tape), focusing and refocusing of the microscope is not necessary, and consequently, the adhesive area can be scanned rapidly.

5. The associated printed grid helps to keep track of the areas examined and aids in identifying the location of matching fibers because the field of view of a stereo light microscope will usually cover an entire square of the grid at sufficiently high magnification ($\times 20$). This feature results in rapid scanning and localization of matching fibers.

6. Unlike the individual strips of tape used in tape lifts, the present device will not easily tear, fold, or become entangled.

7. The storage, cataloging, and sorting of the fiber collection and storage device in document protectors is simpler and more convenient as compared to narrow adhesive strips.

8. As a result of the convenient handling of the device, removal of matching fibers was relatively easier with the present adhesive bed compared to the individual tape lift method as a result of the convenient handling of the device.

9. The adhesive bed techniques used in the practice of this invention have not only made the laser search and localization of matching fibers possible, but also made the procedure convenient and rapid.

10. The device can also be used in the field by the crime scene processing personnel. The success of any criminal investigation is often dependent upon recovery of trace evidence material for subsequent analytical or comparative examinations or both. Textile fibers are one of the most common types of transfer evidence encountered in forensic science. The initial task is to recover the minute fragments of transferred-fibers from the surfaces of the textile articles involved in an incident. An ideal method should be simple, rapid, efficient, and reliable. By using the fiber collection device of this invention which utilizes adhesive bed technique, all these criteria for the collection and recovery of fibers are satisfied. The advantages of this new technique over existing methods, include rapid collection of fibrous evidence material from large apparel surfaces, convenient handling and storage of samples and rapid recovery of suspect fibers. This technique is time-saving and practical in routine cases and meets the needs of over-burdened crime laboratories.

The principle application of the device (adhesive bed) will be in the collection and recovery of fibrous evidence. However, it is contemplated that this device can be used for the collection of physical evidence such as synthetic or natural (i.e. hair) fibers, particles and residues, etc. Some of the major routine uses of the above device will be in (a) crime scene processing in the field, and (b) crime investigation laboratories for the collection and recovery of hairs and/or fibers from textile articles involved in a crime.

The adhesive bed technique offers a single step procedure for each stage of collection, search and localization, and recovery. Also, the fibers collected do not come in contact with other surfaces (other than the clean clear plastic of the document protector or plastic covering sheet). Thus, the integrity and reliability of the evidence is maintained during storage.

BRIEF DESCRIPTION OF THE DRAWINGS

FIG. 1 presents a sketch of the fiber collection and storage device preprinted with grid and label 2, and its associated clear plastic covering 3 attached to the thin layer of adhesive material on the grid area.

DETAILED DESCRIPTION OF THE INVENTION

Figure 2:
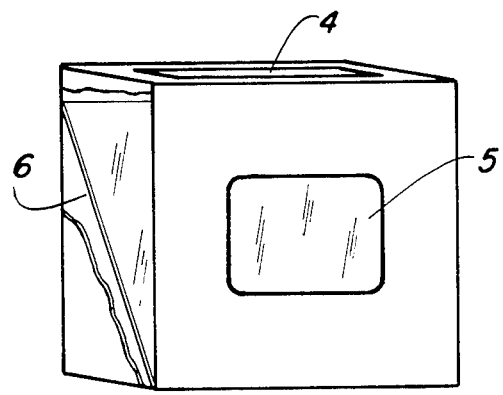
FIG. 2 shows a cutaway view of a fiber luminescence viewing box which has an opening 5 through which the laser beam is directed on to a mirror 6.

A fiber collection and storage device according to this invention broadly can be described as comprised of three essential components: (1) a stable, transparent carrier base material preprinted with a grid and label, said grid having uniquely identified areas wherein collected fibers are located and said label providing identification indicia, (2) an adhesive layer which is disposed on the surface of the carrier base material, said adhesive layer being capable of collecting and recovering transferred-fibers from textile articles, the grid area bearing the adhesive coating identified by reference number "1" in FIG. 1; and (3) a transparent and flexible cover means for occlusively covering said adhesive layer. The carrier base material of the device is preferably a polyester film, having a total size dimensions of approximately 100 by 130, 77 by 95, 100 by 95, 115 by 95, or 215 by 95 millimeters. When the dimensions of the carrier base material is about 100 by 130 millimeters, the size of the grid portion by the film is preferably about 100 by 100 millimeters, the remaining portion of the carrier base, the label portion 2, then being about 30 mm long and 100 mm wide. However, it is understood that the selection of desired dimensions of the fiber collection and storage device may vary within broad limits which facilitate coverage of large surface areas, and the dimensions selected by applicant are illustrative without any implied limitations. The device has alphanumeric characters along the vertical and horizontal axis of the grid which provides a means for uniquely identifying each discrete area on the grid.

The novel device of this invention is used by placing the adhesive surface in contact with a textile surface, thereby causing any transferred fibers to be collected onto the adhesive surface. Once collected, the transferred fibers can be stored by covering the adhesive surface which contains the fibers with the flexible and transparent occlusive cover.

A simple, rapid, and efficient technique for the collection, search, localization, and recovery of fiber evidence is described. The technique appears to be ideal for routine casework.

METHODS AND MATERIALS

Preparation of Adhesive Bed

Transparent polyester film (James River Graphics, South Hedley, Miss.; KBK-P; thickness 0.004 in. [0.01016 cm]) was cut into 100- by 130-mm pieces. The cut film was printed with a 100- by 100-mm grid, divided into 10-mm squares, and labelled with a Xerox copying machine (FIG. 1). The sheets (four or more, depending on the size of the glass plate) were affixed to a glass plate (by using two strips of double coated Scotch ® tape), and the grids were covered with Double Coated ® adhesive tape (1 in. [2.54 cm], 3M, stock No. 665) in such a way that each strip joined the next to form a continuous adhesive bed. The tape along the sides of the grid area were cut by using a surgical knife and the sheets with adhesive bed on one side were carefully lifted from the glass plate and stored in clear plastic 9- by 11-in. [23- by 28-cm] document protectors. Adhesive beds of other sizes were similarly prepared for use with smaller or larger textile surfaces. These beds can be routinely prepared by non-technical laboratory personnel with minimal training.

Collection of Fibers

The fabric article to be examined was placed on a clean sheet of paper and all visible types of evidence, such as hair, fibers, vegetable substances, and so forth, were removed using forceps as suggested by Pounds, C. A., "The Recovery of Fibers from the Surface of Clothing Submitted for Forensic Examination," *Journal of Forensic Sciences*, Vol. 15, No. 2, April 1975, pp. 127–132 and De Forest, P. R., Gaensslen, R. E., and Lee, H. C., *Forensic Science: An Introduction to Criminalistics*, McGraw-Hill, New York, 1983, pp. 146–152. The adhesive device was removed from the document protector and placed over an area of the garment from which the fibers were to be collected. Mild to moderate pressure was applied (depending upon the fabric texture). The device was lifted and applied to an adjacent area of the fabric and the procedure repeated until all of the area under investigation was processed or the adhesiveness of the bed diminished considerably or both. Pertinent information was then recorded on the preprinted label and the device was stored in the document protector.

Search and Localization of Potential Matching Fibers

Two optical systems were used to search and localize the suspected fibers collected by the adhesive device: (1) stereo light microscopy and (2) laser illumination. In both cases, the adhesive bed was examined without removing it from the document protector. Suspect fibers were searched and localized by using a standard stereo light microscope. The scanning of the adhesive surface was carried out with the adhesive surface of the device facing downward and still attached to one side of the document protector.

Figure 3:
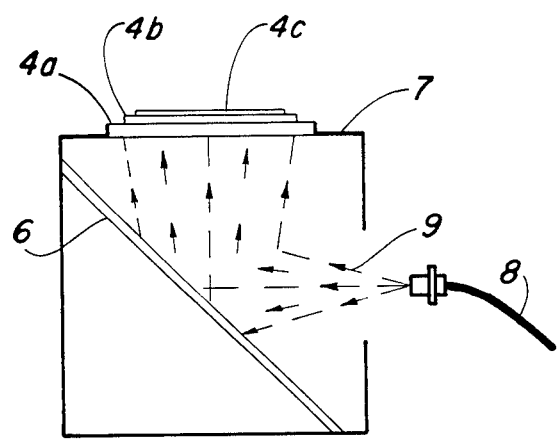
FIG. 3 illustrates laser illumination of the adhesive bed by placing an adhesive bed 4c, a document protector 4b and glass plate 4a on top of the luminescence viewing box, these elements being collectively identified by reference numeral "4" in FIG. 2.

If the known (control) fabric fibers fluoresced by laser illumination, then the adhesive device was searched by the laser beam and suspect fibers were marked (using a Pilot marker pen) by encircling them directly on the nonadhesive side of the device. The laser illumination system consisted of a beam 9 of modest energy (5 W) emitted by a laser (Spectra-Physics argon ion laser, model 171-19) and directed from one side of a wooden box, designated by reference numeral "7" in FIG. 3, (400 by 400 by 400 mm) to a mirror placed at 45° in the box (FIG. 2) such that the reflected beam impinged upon the glass plate on which the document protector containing the adhesive bed was placed (FIG. 3). The laser used may be one where light is transmitted using an optical fiber 8 as illustrated in FIG. 3. Safety goggles (Laser-Guard ® for use with argon lasers; optical density (OD) 15 at 488 nm and 11 at 514.5 nm, luminous transmittance 59%; Glendale Optical Company, Woodbury, N.Y.) were used during search and localization process by laser illumination.

Recovery of Matching Fibers

After localization either by stereo light microscopy or by laser illumination, the suspect fibers were removed from the adhesive bed with fine forceps while constantly viewing and scanning the device under the microscope. These recovered fibers were preserved on microscope slides for additional examination by means of polarizing microscopy or other comparative methods or both.

Results and Discussion

The process of making the adhesive beds of different sizes was quite rapid and simple. Although adhesive beds of several sizes were made (for small and large size clothing articles), the standard size bed (100 by 130 mm) was found to be appropriate for small surfaces (shorts, underpants, brassieres, and so forth) as well as larger surfaces. The device was tested in actual caseworks for the collection and recovery of foreign fibers.

The adhesive bed technique employed in the practice of this invention is simple, effective, practical, and time-saving. The advantages of this technique over previously described procedures are as follows:

1. Since the present fiber collection device and storage has a large surface, each contact with the textile material covers a large area (as compared to using narrow strips of adhesive tape). Thus, a large piece of clothing is processed rapidly and completely. The chances of leaving out unexplored areas will be much lower than would exist if individual strips of adhesive tape were used. Further, in the case of articles with coarse texture, collection of fibers will not be a problem (compared to the individual tape lift method) since appropriate pressure can be applied to recover the suspect fibers from such areas.

2. Since the Double Coated ® tape used is comparable to the conventionally used 3M Scotch 810 Magic tape in adhesive thickness and material, the problem of picking up a greater number of background fibers during collection does not arise.

3. Because the adhesive devices are transparent, the search for matching fibers is relatively easy and rapid.

4. Since the present device stays flat (as compared to the individual strips of adhesive tape), focusing and refocusing of the microscope is not necessary, and consequently, results in rapid scanning of the adhesive area.

5. The associated printed grid helps to keep track of the areas examined and aids in the identification of the location of matching fibers, as the field of view of a stereo light microscope will usually cover an entire square of the grid at sufficiently high magnification (×20). This also results in rapid scanning and localization of matching fibers.

6. Unlike the individual strips of tape used in tape lifts, the present device will not easily tear, fold, or get entangled.

7. The storage, cataloging, and sorting of the adhesive beds in document protectors is simpler and more convenient as compared to narrow adhesive strips.

8 Removal of matching fibers was relatively easier with the present adhesive bed compared to the individual tape lift method as a result of the convenient handling of the device.

9. The adhesive bed technique has not only made the laser search and localization of matching fibers possible but also made the procedure convenient and rapid.

10. The device can also be used in the field by the crime scene processing personnel.

SUMMARY

The fiber collection and storage device of this invention offers a single step procedure for each stage of collection, search and localization, and recovery. Also, the fibers collected do not come in contact with other surfaces (other than the clean clear plastic of the document protector). Thus, the integrity and reliability of the evidence is maintained. In the light of these advantages, applicant believes that the new adhesive bed technique is highly valuable, time-saving, and practical for laboratories with high case loads.

I claim:

1. A fiber collection and storage device comprising in combination:
    (a) a stable, transparent carrier base material preprinted, on a surface thereof, with a grid and label, said grid having uniquely identified areas wherein collected fibers are located and said label providing identification indicia;

(b) an adhesive layer which is disposed on the surface of the carrier base material, said adhesive layer being capable of collecting and recovering transferred-fibers from textile articles; and (c) a transparent and flexible cover means for occlusively covering said adhesive layer.

2. The device of claim 1 wherein the carrier base material is a polyester film.

3. The device of claim 2 wherein the size of the polyester film is about 100 millimeters by 130 millimeters in area.

4. The device of claim 3 wherein said grid is about 100 millimeters by 100 millimeters in area.

5. The device of claim 4 wherein alphanumeric characters along a vertical and a horizontal axis of the grid provides a unique identification of each discrete area on the grid.

6. A method for the rapid collection and recovery of fragments transferred fibers from a surface of textile articles comprising applying to the textile surface a fiber collection and storage device comprised of:

(a) a stable, transparent carrier base material preprinted, on a surface thereof, with a grid and label, said grid having discrete areas for displaying the location of collected fibers and the label providing identification indicia;

(b) an adhesive layer which is disposed on the surface of the carrier base, said adhesive layer being capable of collecting and recovering transferred fibers from textile articles; and (c) a transparent and flexible cover means for occlusively covering said adhesive layer, said method further comprising removing the cover from the adhesive layer before the application step and restoring the cover so that it exclusively covers the adhesive layer after the application step.

7. The method of claim 6 wherein the carrier base material is a polyester film.

8. The method of claim 7 wherein the polyester film is about 100 millimeters by 130 millimeters in area.

9. The method of claim 8 wherein said grid is about 100 millimeters by 100 millimeters in area.

10. The method of claim 9 wherein alphanumeric characters along a vertical and a horizontal axis of the grid provides a unique identification of each discrete area on the grid.

* * * * *